(12) United States Patent
Blixt

(10) Patent No.: US 6,512,143 B1
(45) Date of Patent: Jan. 28, 2003

(54) SALTS OF N-TERT-BUTYLHYDROXYLAMINE

(75) Inventor: Jörgen Blixt, Södertälje (SE)

(73) Assignee: AstraZeneca AB, Sodertalje (CH)

(*) Notice: Subject to any disclaimer, the term of this patent is extended or adjusted under 35 U.S.C. 154(b) by 0 days.

(21) Appl. No.: 09/380,458

(22) PCT Filed: Jul. 6, 1999

(86) PCT No.: PCT/SE99/01228
§ 371 (c)(1),
(2), (4) Date: Sep. 2, 1999

(87) PCT Pub. No.: WO00/02848
PCT Pub. Date: Jan. 20, 2000

(30) Foreign Application Priority Data

Jul. 10, 1998 (SE) .................................................. 9802507

(51) Int. Cl.$^7$ .......................... C07C 53/10; C07C 51/42; C07C 239/00; C07C 259/00; C07B 53/00
(52) U.S. Cl. ...................... 562/607; 562/606; 562/608; 564/301; 564/300
(58) Field of Search ................................ 564/301, 300; 562/606, 607, 608; 554/108

(56) References Cited

U.S. PATENT DOCUMENTS 1,390,260 A * 9/1921 Sulzberger
2,132,454 A * 10/1938 Bassford
2,483,252 A * 9/1949 Tryon
2,950,954 A * 8/1960 Mador et al.
3,325,523 A * 6/1967 Albert

FOREIGN PATENT DOCUMENTS

EP 0217269 4/1987

OTHER PUBLICATIONS

J. Am. Chem. Soc, 1957, 79, 5739–5754.
Tetrahedron Letters, 1973, 21, 1807–1810.
Aldrich Chemical Catalog, 2001 Edition, p. 312.

* cited by examiner

Primary Examiner—Paul J. Killos
Assistant Examiner—Mahreen Chaudhry
(74) Attorney, Agent, or Firm—White & Case LLP

(57) ABSTRACT

Novel salts of N-tert-butylhydroxylamine with lower carboxylic acids are disclosed, together with processes for their preparation. The salts possess advantageous properties that render them useful in synthesis.

8 Claims, No Drawings

SALTS OF N-TERT-BUTYLHYDROXYLAMINE

FIELD OF THE INVENTION

This invention relates to novel salts of N-tert-butylhydroxylamine and processes for their preparation. The salts are useful as intermediates in organic synthesis.

BACKGROUND OF THE INVENTION

N-Alkyl hydroxylamines, including N-tert-butylhydroxylamine, are important as intermediates in organic synthesis, particularly in the preparation of nitrones, hydroxamic acids and C-nitroso compounds (J. S. Roberts in D. H. R. Barton and W. D. Ollis, *Comprehensive Organic Chemistry*, Volume 2, pages 196–201, Pergamon Press, 1979).

Methods for the synthesis of N-alkyl hydroxylaimnes are well known in the art (J. S. Roberts in D. H. R. Barton and W. D. Ollis, *Comprehensive Organic Chemistry*, Volume 2, pages 185–194, Pergamon Press, 1979). The most common method for the synthesis of such compounds involves the reduction of a corresponding nitrogen-containing compound which is at a higher oxidation level than the hydroxylamine itself. Thus, reductions of nitro, nitroso and oxime derivatives have all been used.

W. D. Emmons (*J. Amer. Chem. Soc.*, 1957, 79, 5739–5754) describes the preparation of various oxaziridines by oxidation of the corresponding imine derivative with peracetic acid. Further hydrolysis of these oxaziridines with aqueous acid provides a useful alternative route for the preparation of N-alkyl hydroxylamines.

In a related process, N-alkyl hydroxylamines such as N-tert-butylhydroxylamine may be prepared by oxidation of an imino ether with peracid and subsequent hydrolysis of the resultant alkoxyoxaziridine (D. Thomas and D. H. Aue, *Tetrahedron Letters*, 1973, 1807–1810).

Hydroxylamines are basic compounds and form salts with mineral acids, for example, hydrogen chloride and hydrogen bromide. Salts with strong organic acids, for example, oxalic acid and trifluoromethanesulphonic acid, are also known.

As the free bases, N-alkyl hydroxylamines are not, in general, particularly stable, being prone, for example, to undergo aerial oxidation. For this reason, it is expedient to be able to prepare the generally more stable acid addition salts of such compounds. Such salts are particularly convenient as a means of storage of N-alkyl hydroxylamines.

Bayer (DE 35 35 451; EP 0 217 269) describe a process for the preparation of N-alkyl-substituted hydroxylammonium chlorides by the reaction of certain arylaldimines with perpropionic acid and subsequent hydrolysis of the oxaziridine formed thereby. Such hydrochloride salts are regarded as being particularly advantageous. Thus, it is stated that salts other than the hydrochlorides, for example, the corresponding sulphates or hydrogen sulphates, often crystallise only poorly or not at all, a factor which considerably complicates their preparation, isolation and handling.

It has now surprisingly been found that N-tert-butylhydroxylamine forms stable salts with lower carboxylic acids, for example, with acetic acid. Such salts display advantageous properties and are the subject of the present application.

DISCLOSURE OF THE INVENTION

According to the invention we provide a salt of formula (I)

(CH$_3$)$_3$CNHOH.RCO$_2$H     (I)

wherein:
R represents hydrogen or C 1 to 4 alkyl.

In particular, it is preferred that R represents methyl such that the compound of formula (I) is N-tert-butylhydroxylammonium acetate.

Unless otherwise indicated, the term "C 1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl.

According to the invention, we further provide a process for the preparation of salts of formula (I) which comprises reaction of N-tert-butylhydroxylamine, (CH$_3$)$_3$CNHOH, with a lower carboxylic acid, RCO$_2$H, wherein R is as defined above.

In one aspect of this process, a solution of N-tert-butylhydroxylamine, either formed by liberation of the free base from a salt such as the hydrochloride, or generated directly by synthesis, in a suitable solvent such as ethyl acetate, isopropyl acetate, n-butyl acetate, diisopropyl ether, or methyl t-butyl ether is treated at a suitable temperature with an appropriate amount of a lower carboxylic acid such as acetic acid.

In a preferred aspect, ethyl acetate and sodium acetate, are added to a solution of N-tert-butylhydroxylammonium chloride in water.

In another preferred aspect, ethyl acetate, acetic acid and sodium hydroxide, are added to a solution of N-tert-butylhydroxylamine hydrochloride in water.

In either way, N-tert-butylhydroxylammonium acetate is generated in situ, and may be isolated by separation of the organic (ethyl acetate) layer, followed by evaporation.

It is particularly surprising and advantageous that the novel salt, N-tert-butylhydroxylammonium acetate, can be partitioned from an aqueous phase into an organic phase.

The novel salts of formula (I) may, if necessary, be purified using techniques that are well known in the art. Thus, they may be recrystallised from a suitable solvent such as toluene or ethyl acetate, or from a suitable solvent mixture.

However, most surprisingly and advantageously, the novel salt, N-tert-butylhydroxylammonium acetate, may also be purified by distillation under reduced pressure.

N-tert-butylhydroxylamine, (CH$_3$)$_3$CNHOH, is well known in the literature and may be prepared by methods that are known per se.

Thus, N-tert-butylhydroxylamine may be produced by reduction of 2-methyl-2-nitropropane, (CH$_3$)$_3$CNO$_2$, with, for example, zinc or aluminium amalgam (J. March, *Advanced Organic Chemistry*, 1985 (3$^{rd}$ edition), pages 1103–1104; *Organic Syntheses*, vol. 52, 77–82). For process scale work, such methods suffer from the disadvantages that the 2-methyl-2-nitropropane required as a starting material is itself relatively expensive to prepare, and the reduction process requires careful control not least because of its potentially very exothermic nature.

N-tert-Butylhydroxylamine may also conveniently be prepared using the general methodology described by Emmons (vide infra) as summarised in Scheme 1$^-$. R$^1$ therein may conveniently represent hydrogen, but may also represent one or more other suitable substituents. According to the Scheme, N-tert-butylamine (2) is reacted with a benzaldehyde (3) to give the imine (4) which in turn is oxidised with a peracid to afford the oxaziridine (5). The oxaziridine (5) may then either be hydrolysed directly using aqueous acid or alternatively may be first rearranged to the nitrone (6) which is then itself hydrolysed. In either case the hydrolysis yields a mixture of N-tert-butylhydroxylamine (7), as a salt, and the benzaldehyde (3) which may be readily separated. Advantages of this process are that both of the starting materials (2) and (3) are relatively inexpensive. Furthermore, the benzaldehyde (3) is regenerated in the course of the final hydrolysis and may conveniently be separated and recycled. In addition, if a peracid such as meta-chloroperbenzoic acid is used for oxidation of the imine, the meta-chlorobenzoic acid generated therefrom may also be recovered and subsequently re-oxidised.

Scheme 1

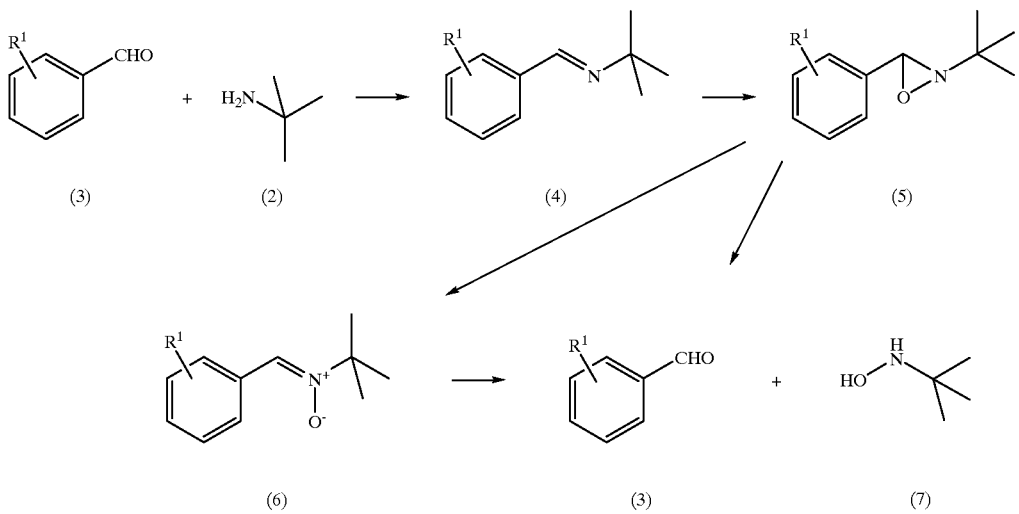

The novel salts of formula (I) are, in general, crystalline compounds which, unlike the corresponding free base, N-tert-butylhydroxylamine, exhibit good stability upon storage, particularly towards aerial oxidation.

If required, N-tert-butylhydroxylamine may be liberated from the salts of formula (I) simply by treatment with base.

When compared to N-tert-butylhydroxylammonium chloride, the novel salts of formula (1) have the particular advantage that they possess a surprisingly greater stability towards heat. Thus, investigation of N-tert-butylhydroxylammonium chloride using differential scanning calorimetry showed that this salt undergoes an extremely exothermic process (ΔH=−1312 J/g) at an onset temperature of +136° C. In contrast, N-tert-butylhydroxylammonium acetate undergoes no significantly exothermic processes when treated under the same conditions.

In addition, N-tert-butylhydroxylammonium chloride is rather hygroscopic, readily taking up water from the surroundings. This disadvantage is much less apparent with N-tert-butylhydroxylammonium acetate.

The invention is illustrated by the following non-limiting examples.

NMR spectra were recorded on a Bruker instrument at 200 MHz for $^1$H and 50 MHz for $^{13}$C. Chemical shift data are given in ppm downfield from tetramethylsilane (TMS).

EXAMPLE 1

N-tert-Butylhydroxylammonium Acetate

N-tert-Butylhydroxylamine hydrochloride (56 g, 0.43 mol, 97%) was dissolved in water (226 g) and charged to a 1 L three-necked glass bottle under argon gas. Ethyl acetate (246 g) and potassium carbonate (79 g, 0.57 mol, 1.3 equiv.) were added and the mixture was stirred vigorously for 1 h at +20° C. Both phases were siphoned to a separating funnel. The water phase was separated off and extracted once more with ethyl acetate (100 ml). The organic phases were pooled and acetic acid (28.1 g, 0.47 mol, ⁻1.09 equiv.) was added. The solvent was evaporated off. The resulting clear, yellow-green oil was treated with additional ethyl acetate (203 g) and concentrated again. The bottle was placed in the refrigerator and after 2 h the product had turned crystalline. The substance was easily crushed giving a slightly yellowish powder (63.4 g, 90%). This material could be recrystallised using either toluene or ethyl acetate as solvent. Differential scanning calorimetry showed an endothermic melting point at +67.7° C. Powder X-ray diffraction analysis showed a high degree of crystallinity.

$^1$H NMR (d$_3$-acetonitrile) δ8.33 (s, 2H), 1.92 (s, 3H) and 1.21 (s, 9H). $^{13}$C NMR (d$_3$-acetonitrile) 67 177.5, 57.0, 23.1 and 21.3.

EXAMPLE 2

N-tert-Butylhydroxylammonium Acetate

N-tert-Butylhydroxylamine hydrochloride (19.7 g, 98%, 0.15 mol) was dissolved in water (40 g) at +20° C. Ethyl acetate (118 g) and sodium acetate (19.3 g, 0.24 mol, 1.5 equiv.) were added. A slurry was formed initially but then dissolved. After 2 h the bluish organic phase was separated and concentrated giving an opaque, yellow oil (20.6 g, 88%) that solidified upon standing in the refrigerator. Chromatographic purity (GC): 97.0 area %.

EXAMPLE 3 a) N-Benzylidene-tert-butylamine

Toluene (330 g), benzaldehyde (66.0 g, 0.62 mol) and tert-butylamine (50.0 g, 0.68 mol, 1.1 equiv.) were added to a 1L reaction bottle connected to a Dean-Stark trap. The bottle was heated in a PEG 400 oil bath maintained at 130° C. After 7 h at reflux, GC indicated that 99.7% conversion had been achieved. The reaction mixture was cooled and used directly in the subsequent step.

In a separate experiment the product was isolated by evaporation and was characterized as follows: Chromatographic purity (GC): 0.2 area % benzaldehyde; 99.8 area % N-benzylidene-tert-butylamine.

$^1$H NMR (CDCl$_3$) δ1.29 (s, 9H), 7.37 (m, 3H), 7.73 (s, 2H) and 8.26 (s, 1H). $^{13}$C NMR (CDCl$_3$) δ29.6, 57.1, 127.8, 128.4, 130.0, 137.1 and 155.0. MS $^m$/z 146 (M$^+$–15, 100%), 161 (M$^+$, 6%).

b) 2-tert-Butyl-3-phenyloxaziridine

Sodium carbonate (65.6 g, 0.62 mol, 1 equiv.) was dissolved in water (400 g) and cooled to +20° C. Meta-Chloroperbenzoic acid (149.8 g, 75%, 0.65 mol, 1.05 equiv.) was dissolved in toluene (300 g) and ethanol (150 g) and heated gently to +20° C. The aqueous sodium carbonate solution was then added to the toluene solution of N-benzylidene-tert-butylamine prepared in (a) above in a 2 L reaction bottle which was immersed in a cold water bath (temperature <+10° C.). The meta-chloroperbenzoic acid solution was then added slowly at +20° C. over 30 minutes. GC analysis showed that complete conversion had been achieved 30 minutes after addition of the meta-chloroperbenzoic acid solution was complete. The water phase was then discarded and the organic phase was filtered through a glass-filter and transferred directly into the following reaction step. In a separate experiment the product was isolated and characterized as follows: Chromatographic purity (GC): 1.9 area % benzaldehyde, 98.1 area % 2-tert-butyl-3-phenyloxaziridine.

$^1$H NMR (CDCl$_3$) δ1.17 (s, 9H), 4.68 (s, 1H) and 7.33–7.46 (m, 5H). $^{13}$C NMR (CDCl$_3$) δ25.2, 58.3, 73.5, 127.4, 128.3, 129.6, 133.2 and 135.5. MS $^m$/z 57 (100%), 177 (M$^+$, 1%).

c) N-tert-Butylphenylnitrone

The reaction mixture from the step (b), approximately 600 ml, was placed in a 1 L reaction bottle fitted with a Dean-Stark trap and heated in a PEG 400 oil bath (+130° C.) overnight (13 h). According to GC, no oxaziridine then remained. The dark brown solution was cooled to +20° C. using a cold water bath (temperature <+10° C.) and was then filtered through K200 filter paper. The filtrate was evaporated on the rotavapor (+50° C.) to leave a dark red-brown oil (93.9 g). The oil crystallized almost immediately.

$^1$H NMR (CDCl$_3$) δ1.61 (s, 9H), 7.38–7.55 (m, 3H), 7.55 (s, 1H) and 8.27–8.32 (m 2H). $^{13}$C NMR (CDCl$_3$) δ28.2, 70.6, 128.2, 128.6, 129.9 and 130.9. MS $^m$/z 57 (100%), 177 (M$^+$, 19%).

d) N-tert-Butylhydroxylammonium Acetate

N-tert-butylphenylnitrone (44.8 g, 0.25 mol) was dissolved in toluene (134 g) in a 500 ml bottle. Sulphuric acid (27.5 g, 95 to 97%, 0.27 mol, 1.1 equiv.) was diluted in water (134 g) and added to the reaction bottle. The two-phase mixture was then heated to +50° C. and stirred vigorously for approximately 2 h. At that time, GC indicated that only 0.2 area % of N-tert-butylphenylnitrone remained. After cooling to +20° C., the dark red organic phase was discarded and the clear, yellow water phase was extracted once with toluene (46 g). To the remaining water phase was then added acetic acid (14.8 g, 0.25 mol, 1.0 equiv.) followed by sodium hydroxide (45% aqueous solution) until the pH of the water phase was approximately 5.5. Ethyl acetate (224 g) was then added and the mixture was stirred vigorously. The organic phase was then separated and the aqueous phase was extracted once more with ethyl acetate. The combined organic fractions were then evaporated to leave an oil (35.2 g). This material was purified by distillation under reduced pressure. A stable distillation point was achieved at 19 mbar/ +78° C. Fraction 1, retrieved below +70° C., contained 2.7 g and fraction 2, collected between +70° C. and +80° C., con a highly viscous oil (28.7 g, 76%) that crystallized as a white solid upon standing. pKa 6.4 Chromatographic purity (GC): 99.4 area %

$^1$H NMR (d$_4$-methanol) δ1.27 (s, 9H), 1.95 (s, 3H) and 5.51 (s, NO-H). $^{13}$C NMR (d$_4$-methanol) 67 22.9, 24.1, 59.0 and 180.2.

EXAMPLE 4

N-tert-Butylhydroxylammonium Acetate 2-tert-Butyl-3-phenyloxaziridine (30.3 g, 98.2 area %, 0.17 mol) was dissolved in ethanol (90 g). Sulphuric acid (25.7 g, 95 to 97%, 0.25 mol, 1.5 equiv.) was diluted in water (90 g) and added to the 500 ml reaction bottle. The reaction mixture was stirred at +20° C. for 20 h at which time analysis by GC showed that 5.8 area % oxaziridine remained. Leaving the reaction stirring over the weekend gave complete conversion. The solvents were evaporated and the concentrate was partitioned between water (90 g) and ethyl acetate (90 g). The organic phase was discarded and fresh ethyl acetate (150 g) and acetic acid (10.8 g, 0.18 mol, 1.1 equiv.) were added, followed by sodium hydroxide (45% aqueous solution) until the aqueous phase had approximately pH 5.5. The organic phase was then separated, filtered through K200 filter paper and concentrated giving an oil (17.3 g). This material was distilled at 20 mbar and the fractions distilling above +72° C. were collected giving a clear oil (11.5 g, 45%) that crystallized immediately. Chromatographic purity (GC): 99.5 area %

What is claimed is:

1. A salt of formula (I)

$$(CH_3)_3CNHOH.RCO_2H \qquad (I)$$

wherein R represents hydrogen or C 1 to 4 alkyl.

2. A salt according to claim 1 which is N-tert-butylhydroxylammonium acetate.

3. A process for the preparation of a salt according to claim 1 which comprises reaction of N-tert-butylhydroxylamine, (CH$_3$)$_3$CNHOH, with a lower carboxylic acid, RCO$_2$H, wherein R is as defined in claim 1.

4. A process for the preparation of N-tert-butylhydroxylamine acetate which comprises reaction of a solution of N-tert-butylhydroxylamine, (CH$_3$)$_3$CNHOH, in a suitable solvent with acetic acid.

5. A process for the preparation of N-tert-butylhydroxylamine acetate which comprises treatment of a solution of N-tert-butylhydroxylammonium chloride in water with sodium acetate in the presence of ethyl acetate.

6. A process for the preparation of N-tert-butylhydroxylamine acetate which comprises treatment of a solution of N-tert-butylhydroxylammonium chloride in water with acetic acid and sodium hydroxide in the presence of ethyl acetate.

7. A process for the isolation of N-tert-butylhydroxylamine acetate prepared according to claim 5 or claim 6 which comprises:
   a) extraction of the N-tert-butylhydroxylamine acetate from an aqueous environment into an ethyl acetate layer;
   b) separating the ethyl acetate layer; and
   c) removing the ethyl acetate by evaporation.

8. A process for the purification of N-tert-butylhydroxylamine acetate which comprises distillation under reduced pressure.

* * * * *